United States Patent [19]
Dacruz

[11] Patent Number: 5,266,496
[45] Date of Patent: Nov. 30, 1993

[54] HEADSPACE ANALYSIS

[76] Inventor: Amelia L. Dacruz, 3750 Chesterfield Ave., Virginia Beach, Va. 23455

[21] Appl. No.: 866,359

[22] Filed: Apr. 10, 1992

[51] Int. Cl.$^5$ ................... G01N 25/00; G01N 25/14
[52] U.S. Cl. ........................... 436/157; 73/19.01; 73/19.1; 73/23.41; 73/863.12; 436/30; 436/146
[58] Field of Search ............. 436/157, 30, 31, 32, 436/146; 422/80, 68.1; 73/19.01, 19.02, 19.1, 863.12, 23.41

[56] References Cited

U.S. PATENT DOCUMENTS

| | | | |
|---|---|---|---|
| 2,165,440 | 7/1939 | Bays | 73/19.09 |
| 2,212,681 | 8/1940 | Dunn | 73/19.09 |
| 2,227,438 | 9/1938 | Campell | 436/31 |
| 2,711,644 | 6/1955 | Myers | 73/19.09 |
| 2,749,220 | 6/1956 | Rocmon | 73/19.09 |
| 2,799,561 | 7/1957 | Rocmon | 73/19.09 |
| 3,418,841 | 12/1968 | Issenmann | 73/19.09 |
| 3,539,299 | 11/1970 | Thompson | 436/32 |
| 3,892,528 | 7/1975 | Fredericks | 436/157 |
| 3,937,060 | 2/1976 | Lewis et al. | 73/19.05 |
| 3,953,171 | 4/1976 | Espitalie et al. | 436/157 |
| 4,096,734 | 6/1978 | Khayat | 73/23.41 |
| 4,229,181 | 11/1980 | Espitalie et al. | 436/31 |
| 4,816,412 | 3/1989 | Schmidt et al. | 436/32 |

FOREIGN PATENT DOCUMENTS 2029014 3/1980 United Kingdom .

OTHER PUBLICATIONS

Eggimann et al.; "Decomposition and Analysis of refractory Oceanic Suspended Materials"; Analytical Chemistry; vol. 48, No. 6, May 1976.

Krishnamurty et al.; "Trace metal extraction of solid and sediments by Nitric Acid-Hydrogen Peroxide"; Atomic Absorption Newsletter, vol. 15(3), May 1976.

*Primary Examiner*—James C. Housel
*Assistant Examiner*—Ramon Torres
*Attorney, Agent, or Firm*—John K. Donaghy

[57] ABSTRACT

A process for extracting and analyzing virtually any sample which may be contaminated with pollutants, toxics or other impurities. The process can be used to extract and analyze one contaminant, such as a volatile compound (gasoline), or the process can be used to extract and analyze several contaminants, including both volatiles and semi-volatiles. The process comprises a vacuum extraction technique followed by a heating-/cooling cycle comprising a series of heating and cooling stages.

19 Claims, No Drawings

HEADSPACE ANALYSIS

The present invention relates to a process for analyzing virtually any sample which may be contaminated with pollutants, toxics or other impurities. The process comprises a vacuum extraction technique followed by a series of heating and cooling stages. The extracted contaminants are injected into a gas chromatography column for analysis. The process is conducted in the absence of any solvents or other hazardous materials during the extraction process and permits analysis of samples containing very low concentrations of contaminants.

BACKGROUND OF THE INVENTION

The analysis of soil and liquid samples for potentially harmful materials has acquired greater importance as environmental awareness grows. One area of significant concern is the contamination of water and soil by petroleum by-products, such as gasoline and diesel fuels. The Environmental Protection Agency has set forth numerous regulations in the last decade, for instance, The Clean Water Act, requiring the testing of water and soil for contamination.

Several tests exist for determining the contamination of soil and/or water by pollutants, toxics and other contaminants, particularly volatiles and semi-volatiles. Such tests can be classified into one of three groupings. The first classification is known as Headspace Screening. In this method, either a solid or liquid sample, suspected of contamination, is placed into a container, such as a glass vial, and is heated to a temperature of about 150° C. Volatile organic compounds are vaporized, escape to the headspace directly above the sample, and are extracted therefrom for analysis. A major deficiency in this method is that the sample must be contaminated to the extent that sufficient analyte be vaporized to the headspace. Hence, in this process, the detection limit is fairly high and samples having very low contamination cannot be adequately analyzed. A second disadvantage with the Headspace Screening method is that the extracted contaminants in the headspace typically rebind and complex with the water and moisture in the sample, thereby making it more difficult to detect low concentration of contaminants.

A second method is commonly referred to as the Purge and Trap Method. In this method, an aqueous sample is prepared from the contaminated source and place in a specially designed purging container at ambient temperature. Volatile organic compounds in the sample are converted from the aqueous phase to the vapor phase by the bubbling of an inert gas through the aqueous sample and swept to a sorbent trap. After purging is completed, the trap is heated and backflushed with the same inert gas to desorb the compound onto a gas chromatographic column whereupon the compounds are analyzed. The primary disadvantage is that the Purge and Trap method is capable of extracting and analyzing primarily light ends of hydrocarbons. Although some heavy ends also are extracted these compounds tend to collect as residual contamination in the trap. A related disadvantage in this method is that the trap must be cleaned with a solvent or changed after each contaminated use in order to cleanse the residual contamination from the trap.

A third method is the simple solvent extraction method, wherein an aqueous sample is admixed with a specific solvent designed to extract a particular analyte. The aqueous sample is shaken and the contaminants are separated from the sample. An essential drawback in this method is the use of solvents which are themselves pollutants of water and soil.

Among the widespread contamination of the water and the land, one of the more worrisome contaminations is caused by petroleum by-products. For instance, two common petroleum by-products typically found contaminating ground water, sludges and soil are gasoline and diesel. Accordingly, a method for Total Petroleum Hydrocarbons (TPH) analysis is required. Currently, TPH analysis cannot be efficiently performed by one simple method. Rather, two individual tests are required: (1) the analysis for volatile hydrocarbons (e.g. gasoline) which can be performed by the Headspace method or the Purge and Trap method and (2) the analysis for semi-volatile hydrocarbons (e.g. diesel) which is performed by the solvent extraction method. Because each of these methods is designed to primarily extract either volatiles or semi-volatiles, the analyst must employ two analytical procedures to determine whether contamination by gasoline and diesel fuels is present.

A number of processes have been disclosed in the prior art regarding extracting hydrocarbon contaminants from soil samples. For example, U.S. Pat. Nos. 2,165,440 and 2,212,681 teach a soil gas analysis wherein a soil sample is analyzed by the application of heat and vacuum in order to remove and sample the gas thereof. In U.S. Pat. No. 2,749,220, a method is disclosed for measuring gas in cones wherein a solid core is subjected to vacuum extraction in an evacuated chamber. Air is then mixed with the extracted gas in the chamber to form an air-gas mixture of known volume, and the proportion of hydrocarbon gas is thereafter determined.

Similarly, U.S. Pat. No. 2,799,561 discloses subjecting a solid core of soil to vacuum extraction in an evacuated chamber wherein a series of vacuum extractions is applied to a core sample which is being maintained under reduced pressure for a period of time following each extraction, in order to permit further volatilization of the liquid hydrocarbons in the sample.

U.S. Pat. No. 3,418,841 to Issenmann also provides a method of measuring and recovering gases from a sample of soil and the like by the use of heat in a vacuum.

In U.S. Pat. No. 3,539,209, a solvent extraction-type method is utilized, wherein earth samples are caused to release their content of hydrocarbon gases for analysis by treatment with a hot ethylenediamine tetraacetic acid solution. In U.S. Pat. No. 4,229,181, a sample of geological sediment is heated in intervals, to a first temperature range of 50°–65° C., a second temperature range of 200°–350° C., and a third and final temperature of 550°–600° C. Distinct hydrocarbons are released at successive stages.

Despite the teachings of the prior art, a need exists for a process for extracting pollutants, toxics and other impurities from virtually any sample wherein said sample can be analyzed for both volatiles and semi-volatiles from the same extraction process.

SUMMARY OF THE INVENTION

It is an object of the present invention to provide a process wherein virtually any sample may be analyzed in the same manner without the need to modify the process for a given sample.

It is another object of the present invention to provide a process for analyzing a sample in the absence of solvents or other hazardous materials.

It is still another object of the present invention to provide a process for analyzing a sample in order to detect contaminants at low concentration.

It is a further object of the present invention to provide a process for analyzing a sample having more than one contaminant, wherein all the contaminants can be extracted and analyzed in the same manner.

It is yet another object of the present invention to provide a process for analyzing a sample wherein the contaminants can be extracted and stored for an indefinite period prior to analysis.

The present invention provides a process for extracting and analyzing virtually any sample which may be contaminated with pollutants, toxics or other impurities. The process can be used to extract and analyze one contaminant, such as a volatile compound (gasoline), or the process can be used to extract and analyze several contaminants, including both volatiles and semi-volatiles. The process comprises a vacuum extraction technique followed by a heating/cooling cycle comprising a series of heating and cooling stages.

DETAILED DESCRIPTION OF THE INVENTION

The present invention relates to a process for analyzing virtually any sample which may be contaminated with pollutants, toxics or other impurities. The method can be utilized with virtually any sample. Such samples can be in either liquid or solid form, or can be mixtures thereof, such as sludges, emulsions, dispersions, suspensions and the like. Illustrative of such samples are soil, wood, rock, mud, ground water, waste water, effluents, brine, petroleum hydrocarbons and by-products thereof, as well as surface waters, such as rivers and streams, lakes and ponds, and ocean water. Additionally, the present process may be employed to determine the concentration of one or more specific materials within a sample. For instance, the process may provide a complete analysis of TPH's, or the process may include the extraction and analyzation of both volatiles and semi-volatiles. The method of the present invention can be used to test for an array of pollutants, toxics, contaminants and other materials, including, Total Petroleum Hydrocarbons (TPH), pesticides, herbicides, polychlorinated biphenyls pcbs, phenols, phthalate esters and hydrophobic solvents and other common substances contaminating the land and water.

The process comprises a vacuum extraction technique followed by a series of heating and cooling stages, hereinafter referred to as the heating/cooling cycle. More particularly, the process comprises placing a sample in an extraction vessel and sealing the vessel; applying a vacuum of 25 mm Hg equivalent over the vessel thereby creating a headspace above the sample; agitating the sample and extraction vessel; subjecting the sample to a heating/cooling cycle; and, immediately following the final heating stage, injecting the gaseous contaminants from the headspace into a gas chromatography column for analysis.

The sample may be either liquid or solid or some combination thereof. The initial sample volume must be determined prior to conducting the present invention. Solely for the purposes of this discussion, the chosen sample volume remains constant, as described hereinafter. It is to be understood that the invention can be practiced with other sample volumes, appropriately corresponding to the volume of the extraction vessel.

The extraction vessel utilized in the present invention may be any glass container which is capable of being sealed for vacuum extraction. Solely for the purposes of this discussion, the glass container used in the process is a 50 ml glass vial comprising a 20 mm septa for capping and sealing the vial (a teflon crimptop). The vial has an actually capacity of approximately 67-68 ml. Accordingly, the sample volume has been chosen to be 25 ml, thereby resulting in a headspace (HS) constant of 37 ml. Generally, if the sample is water, the volume for the sample is 25 ml. Thus, given that the 25 ml volume is extracted into the 37 ml headspace, there is a 1.48 dilution factor for such a sample (the dilution factor being calculated by dividing the HS constant with the sample volume). In cases of other liquid samples wherein the concentration of contamination is believed to be high, a predetermined volume of said sample is place in the extraction vial and diluted to the 25 ml total volume by the addition of deionized (DI) water.

For solid samples, such as samples of soil, rock, wood or the like, a known volume is weighed and diluted with deionized water to achieve a predetermined volume for placement in the extraction vessel. Again, solely for the purposes of this discussion, the solid sample volume is 1.0 grams of the solid, which is brought to a volume of 25 ml with deionized water, thereby resulting in a dilution factor of 37.

In order to prevent the loss of any of the contaminants (or a percentage thereof), the sample may be stabilized, either at the time of collection or prior to placement in the extraction vessel. The cooler the sample, the more stabilized it becomes. Preferably, the sample should be cooled to about 4° C. Indeed, in EPA analysis, it is required that the sample be collected, sealed in a container and quickly refrigerated. In this manner, the sample is neither further contaminated, nor are the contaminants within the sample subjected to further degradation. If the sample has been cooled prior to placement in the extraction vial, then deionized water at a temperature of 4° C. should be used to bring the sample to volume.

Once the sample has been placed in the extraction vessel and brought to volume (that is 25 ml), the extraction vial is sealed, for instance with a clean teflon-lined cap which is crimped over the sample. A vacuum of 25 mmHG equivalent is applied to the sample and extraction vessel for a period of time in the range of from about 30 seconds to about 2 minutes, and preferably about 1.5 minutes. In a preferred method, the vacuum may be executed by placing a leur lock end of a 1000 $\mu$l capacity needle onto a tubing, connected said tubing to a regulated vacuum pump, penetrating the sealed vial with said needle, and timing the withdrawal accordingly. After a predetermined period (e.g. 1.5 minutes), the needle is removed, preferably while the vacuum is still present to eliminate any reverse air entry by way of the tubing. Of course, any method in which vacuum extraction can be achieved may be used without departing from the scope of the present invention. In this manner, the contaminants, including volatiles and semi-volatiles, present in the sample are more likely to expand and escape to the headspace.

It should be understood that once the sample is placed in the extraction vessel, the vacuum should be applied as quickly as possible to ensure that the cooled sample does not become heated, thereby creating an environment favorable to the degradation of the contaminants. One solution to this challenge is to cool the extraction vessel to the same temperature of the cooled sample (such as 4° C.) to lessen the possibility of degradation.

Upon completion of the vacuum operation, the sample is considered to be extracted. At this point, the extracted sample is considered preserved and may be held for an indefinite period prior to being analyzed. Holding times of up to four weeks have been documented without deterioration of the extracted sample. Of course, the holding time may be longer, subject only to the degradation of the contaminants. Moreover, the extracted sample does not have to be refrigerated or cooled for the purpose of maintenance.

In some instances, the extracted contaminants in the headspace may be loosely bound and/or complexed with the water or moisture in the sample. However, this type of bonding is easily broken in the next stage of the process. In order to promote optimum contaminant extraction from the headspace, the extraction vial containing the sample is shaken for from about 1 minute to about 5 minutes, preferable for about one minute. The sample then is subjected to a series of heating and cooling cycles. The sample can be heated to a temperature ranging from about 150° C. to about 200° C., preferably about 165° C. to about 190° C., and most preferably to about 180° C. The cooling temperatures are controlled and limited to typical room temperature ranges, that is, from about 18° C. to about 30° C., and preferably, the sample is cooled to about 20° C. The time for each heating and cooling interval is independent from one another. Each interval can range from about 2 minutes to about 15 minutes, the preferred temperature stage being conducted for a period of about ten minutes. Of course, since time and temperature are mutually dependent, the time of each interval will depend, to some extent, on the temperature used. The number of heating and cooling stages within the heating/cooling cycle also can be varied, with three heating and two cooling stages being an average number. Of course, the cycle begins with a first heating stage and concludes with a final heating stage, and there must be at least one cycle.

Heating the sample at several intervals allows optimum extraction of the contaminants from the headspace, as opposed to prior processes where the sample is heated only once. This optimum recovery is due to the fact that when the samples are cooled between successive heating stages, aqueous vapors are able to return to a liquid state while the more volatile vapors remain in the gaseous state. In this manner, the succeeding heating stage is provided in order to release even more of the analytes of concern into the headspace due to the fact that the aqueous vapors have returned to their former (i.e. liquid) state.

After the final heating stage, an aliquot is extracted from the headspace and immediately injected into a gas chromatography column, such as a DB-1 EPA approved column, for GC analysis. Preferably, a gas sample aliquot in the range of from about 500 μl to about 1,000 μl should be extracted. Obviously, it is only necessary to collect a sufficient amount of the gaseous contaminant to allow adequate analysis in the GC column.

In order to determine an accurate value of the concentration of contamination of the sample, it is necessary to subtract a blank result from the sample result. The blank result is established by periodically analyzing, according to the present process, a 25 ml blank of deionized water. The quality and purity of the blank is, of course, contingent not only on the purity of the water itself, but also on the cleanliness of the sample vials, the syringe and the injection liner. Generally, the injection liner and septa will be changed after every ten injections. The actual result, indicating the actual contamination concentration of the source sample, is thereafter determined by multiplying the dilution factor by the difference between the sample result and the blank result.

The above-described extraction process provides a greatly enhanced recovery method such that 10 ppm appears to be 100 ppm, thereby significantly lowering the detection limit required for sampling. Moreover, this process provides an exceptional extraction method in the absence of solvents and other potentially hazardous materials.

In the preferred embodiment of the present invention, the process comprises the following steps:

(1) obtaining a cooled sample and bringing it to a volume of 25 ml with deionized water which has been cooled to the same temperature of the sample, preferably the temperature of both the DI water and sample are at 4° C.;

(2) placing said cooled sample in an extraction vial and quickly sealing the vial:

(3) immediately applying a vacuum of 25 mmHg equivalent for 1½ minutes by placing into the sample a 1,000 μl capacity needle and tubing, which is connected to a regulated vacuum pump, and timing accordingly;

(4) removing the needle while the vacuum is operative to eliminate any reverse air entry by means of said tubing;

(5) shaking the sample and extraction vial for a period of one minute;

(6) subjecting the sample to a heating/cooling cycle for a predetermined intervals; and (7) immediately following the final heating stage, drawing a gas sample aliquot from the headspace and injecting said sample into a gas chromatography column for analysis.

In this preferred embodiment, the heating/cooling cycle comprises three heating and two cooling cycles, each of which is conducted for an interval of ten minutes.

In an equally preferred alternate embodiment, the cooled sample (brought to 25 ml volume with chilled deionized water at a temperature of 4° C.) is placed in an extraction vessel which has been cooled to the same temperature.

The following examples, which include preferred embodiments, further illustrate the present invention.

EXAMPLE 1

Analysis of Ground Water

A ground water sample from a monitoring well was collected, sealed in a glass container, and chilled to a temperature of 4° C. The water sample was analyzed for Total Petroleum Hydrocarbons (TPH) contamination. 25 ml of ground water, cooled to a temperature of 4° C. was placed in a 50 ml extraction vial having an actually capacity of 68 ml, thereby creating a headspace constant (HS) of 38 ml. The dilution factor (HS/sample volume) was 1.52. A vacuum of 25 mmHg was applied to the extraction vial for 1.5 minutes. Following the vacuum extraction, the vial containing the extracted sample was placed in an oven at temperature of 180° C., and heated for ten minutes. The sample was carefully removed from the oven and cooled to room temperature for ten minutes, reheated in the oven for ten minutes, recooled at room temperature for ten minutes, and finally reheated at 180° C. for ten minutes. Immediately after this final heating stage, a 500 μl sample gas aliquot was drawn from the headspace of the extraction vessel and injected into a DB-1 column for gas chromatographic analysis of the percentage of TPH present in the sample. The GC analysis yielded a sample result of 0.43 ppm of TPH. The actual sample contamination concentration is determined by subtracting the sample result from a previously conducted blank result of 0.08, multiplying by the dilution factor (1.52) thereby yielding an actual ground water TPH contamination concentration of 0.53 ppm.

source samples containing very high concentrations (such as the soil sample tested in Example 14, and the liquid sample tested in Example 9).

TABLE I

| Example | SOURCE | SAMPLE ml/g | HS CONSTANT | DILUTION FACTOR | SAMPLE RESULT | BLANK RESULT | ACTUAL RESULT |
|---|---|---|---|---|---|---|---|
| 3 | soil | 1 gram | 38 | 38 | 2.329 | 0.072 | 85.77 |
| 4 | soil | 1 gram | 38 | 38 | 0.237 | 0.072 | 6.27 |
| 5 | water | 25 ml | 38 | 1.52 | 8.820 | 1.140 | 11.67 |
| 6 | water | 25 ml | 38 | 1.52 | 1.074 | 0.8 | 1.51 |
| 7 | water | 25 ml | 38 | 1.52 | 5.930 | 0.8 | 8.897 |
| 8 | water | 25 ml | 38 | 1.52 | 0.770 | 0.8 | 1.05 |
| 9 | water | 25 ml | 38 | 1.52 | 57.350 | 0.8 | 87.05 |
| 10 | water | 25 ml | 37 | 1.48 | 0.355 | 0.065 | <0.04 |
| 11 | water | 25 ml | 37 | 1.48 | 0.605 | 1.902 | <0.04 |
| 12 | water | 25 ml | 37 | 1.48 | 4.161 | 2.810 | 2.00 |
| 13 | water | 25 ml | 37 | 1.48 | 2.358 | 2.810 | <0.04 |
| 14 | soil | 0.1 gm | 38 | 380 | 43.79 | 0.08 | 16,610.0 |
| 15 | soil | 1 gram | 38 | 38 | 0.89 | 0.08 | 30.84 |

EXAMPLE 2

Analysis of Soil

Soil from an auger boring sample was collected, sealed in a glass container and chilled to 4° C. The sample was analyzed for TPH contamination. A one gram sample of the soil was placed in an extraction vessel having the same dimensions as in Example 1. The sample was brought to 25 ml volume with DI water and cooled to a temperature of 4° C. A vacuum of 25 mmHg was applied to the extraction vial for 1.5 minutes. Following the vacuum extraction, the vial containing the extracted sample was placed in an oven at temperature of 180° C., and heated for ten minutes. The sample was carefully removed from the oven and cooled to room temperature for ten minutes, reheated in the oven for ten minutes, recooled at room temperature for ten minutes, and finally reheated at 180° C. for ten minutes. Immediately after this final heating stage, a 500 μl sample gas aliquot was drawn from the headspace of the extraction vessel and injected into a DB-1 column for gas chromatographic analysis of the percentage of TPH present in the sample. The GC analysis yielded a sample result of 28.81 ppm of TPH, an actual sample result of 28.73 ppm (a blank result of 0.08 ppm), thereby the actual TPH contamination of the soil sample was determined to be 1,091.6 ppm.

The following table shows the results of Examples 3 to 15. Each of these samples was subjected to the same methods employed in Examples 1 and 2 with the same apparatus. Actual Results indicates the actual contamination of the source sample. A review of the data in Table I clearly demonstrates that the process of the present invention can be used for source samples containing very low contamination concentration (such as the liquid samples tested in Examples 10, 11 and 13), and While particular embodiments of the invention have been described, it will be understood, of course, that the invention is not limited thereto, and that many obvious modifications and variations thereof can be made, and that such modifications and variations are intended to fall within the scope of the appended claims.

I claim:

1. A process for extracting and analyzing a sample containing at least one volatile contaminant, comprising the following steps:
    (a) placing a sample in an extraction vessel and sealing the vessel;
    (b) applying a vacuum of 25 mmHg equivalent over the extraction vessel thereby creating a headspace above the sample;
    (c) agitating the sample and extraction vessel;
    (d) subjecting the sample to at least one heating and cooling cycle, wherein said cycle comprises a first heating stage followed by a cooling stage, wherein in said cooling stage, aqueous vapors in the headspace are converted to the liquid state while the volatile contaminant vapors remain in the gaseous state, thereby preventing the complexing of the gaseous contaminants with the aqueous vapors, and wherein after said at least one heating and cooling cycle is conducted, subjecting the sample to a final heating stage; and
    (e) withdrawing a sample gas aliquot from the headspace and injecting said sample into a gas chromatography column for analysis, wherein said withdrawal occurs only after the final heating stage.

2. The process according to claim 1, wherein the sample is a liquid sample.

3. The process according to claim 2, wherein the liquid sample is selected from the group consisting of ground water, waste water, effluents, and surface waters.

4. The process according to claim 1, wherein the sample is a solid sample.

5. The process according to claim 4, wherein the solid sample is selected from the group consisting of soil, wood and rock.

6. The process according to claim 1, wherein the sample is selected from the group consisting of mud, sludges, emulsion, suspensions and dispersions.

7. The process according to claim 1, wherein the sample is contaminated with petroleum by-products.

8. The process according to claim 7, wherein the sample is contaminated by gasoline, diesel, and mixtures thereof.

9. The process according to claim 1 wherein the sample is contaminated with one or more substances selected from the group consisting of pesticides, herbicides, polychlorinated biphenyls (pcbs), phenols, phthalate esters and hydrophobic solvents.

10. The process according to claim 1 further comprising the step of storing and preserving the sample after the vacuum extraction step (b).

11. The process according to claim 1, wherein the sample is initially chilled to a temperature of 4° C.

12. The process according to claim 11, wherein the extraction vessel is chilled to the same temperature as the sample.

13. The process according to claim 1, wherein the sample is chilled and diluted with chilled deionized water to bring the sample to a volume of 25 ml before placement in the extraction vessel.

14. The process according to claim 1, wherein the process comprises one heating and cooling cycle.

15. The process according to claim 14, wherein each temperature stage is independently conducted for an interval of from about 2 minutes to about 15 minutes.

16. The process according to claim 15, wherein each interval is conducted for ten minutes.

17. The process according to claim 14 wherein the process comprises two heating and cooling cycles.

18. The process according to claim 17, wherein each heating stage is conducted at a temperature of from about 150° to about 200° C.

19. The process according to claim 18, wherein each heating stage is conducted at a temperature of about 180° C.

* * * * *